United States Patent [19]

Kwan et al.

[11] Patent Number: 5,314,697
[45] Date of Patent: May 24, 1994

[54] STABLE EXTENDED RELEASE ORAL DOSAGE COMPOSITION COMPRISING LORATADINE AND PSEUDOEPHEDRINE

[75] Inventors: Henry K. Kwan, Summit; Stephen M. Liebowitz, Neshanic Station, both of N.J.

[73] Assignee: Schering Corporation, Kenilworth, N.J.

[21] Appl. No.: 965,470

[22] Filed: Oct. 23, 1992

[51] Int. Cl.⁵ .............................................. A61K 9/36
[52] U.S. Cl. ...................................... 424/480; 424/463; 424/465; 424/468; 424/469; 424/470; 424/474; 424/475; 514/849; 514/853; 514/964; 514/965
[58] Field of Search ............... 424/480, 463, 465, 468, 424/469, 470, 474, 475; 514/849, 853

[56] References Cited

U.S. PATENT DOCUMENTS 4,282,233 8/1981 Vilani .................................. 424/267
4,990,535 2/1991 Cho et al. ............................ 514/556
5,100,675 3/1992 Cho et al. ............................ 424/468

OTHER PUBLICATIONS

Package Label for Claritin ® (Loratadine, 5 mg, pseudoephedrine sulfate, 120 mg) Extra Repetabs Schering, Canada.

Primary Examiner—Paul R. Michl
Assistant Examiner—James M. Spear
Attorney, Agent, or Firm—Thomas D. Hoffman

[57] ABSTRACT

A film-coated extended release oral dosage composition containing the nasal decongestant pseudoephedrine sulfate in a unique polymer matrix core and a film-coating on such core containing the non-sedating antihistamine, loratadine, and use of the said composition for treating patients showing the signs and symptoms associated with upper respiratory diseases and nasal congestion are disclosed.

7 Claims, No Drawings

STABLE EXTENDED RELEASE ORAL DOSAGE COMPOSITION COMPRISING LORATADINE AND PSEUDOEPHEDRINE

BACKGROUND OF THE INVENTION

This invention relates to a film-coated extended release oral dosage composition containing the nasal decongestant pseudoephedrine in a unique polymer matrix core and a film-coating on such core containing the non-sedating antihistamine, loratadine. The oral dosage composition is useful for treating patients showing the signs and symptoms associated with upper respiratory diseases and nasal congestion.

Loratadine is disclosed in U.S. Pat. No. 4,282,233 as a non-sedating antihistamine and it is useful as an anti-allergy agent in, for example, the treatment of seasonal allergic rhinitis symptoms such as sneezing and itching.

Pseudephedrine as well as pharmaceutically acceptable acid additional salts, e.g., those of HCl or $H_2SO_4$, is a sympathomimetic drug recognized by those skilled in the art as a safe therapeutic agent effective for treating nasal congestion and is commonly administered orally and comcomitantly with an antihistamine for treatment of nasal congestion associated with allergic rhinitis. For example, 5 mg of loratadine and 120 mg of pseudoephedrine sulfate ("PES") in a matrix core repetab tablet product is available wherein the PES is equally distributed in the tablet coating and barrier core and all the loratadine is in the coating. The product is recommended for twice-a-day dosing for effectiveness. It would be desirable to have a once-a-day loratadine-pseudoephedrine product.

The successful development of a formulation of a loratadine-pseudoephedrine once-a-day product requires achieving a release rate profile for pseudoephedrine component over an extended period in excess of twelve hours while maintaining the safety and effectiveness of loratadine. Products containing non-sedating antihistamines in combination with pseudoephedrine such as Seldane-D, a press-coated product of terfenadine and pseudoephedrine and Hismanal-D, a combination of pseudoephedrine prills and a separate astemizole tablet are known. However, the administration of terfenadine and astemizole products to humans has been found to cause adverse effects including cardiac arrhythmias and occurrence of these arrhythmias have increased when the terfenadine or astemizole products are co-administered with other drugs such as ketoconazole and erythromycin or upon overdose of the non-sedating anti-histamine.

It would be desirable for increased patient compliance to have an extended release product effective and safe when used on a once-a-day basis.

SUMMARY OF THE INVENTION

We have discovered that a film-coating of loratadine on a core tablet containing pseudoephedrine sulfate in a specific polymer matrix provides immediate release of loratadine and extended release of pseudoephedrine sulfate from the matrix core over a period in excess of twelve hours.

Thus the present invention provides a film-coated extended release oral dosage composition comprising:

a. a matrix core comprising:

|  | mg/core |
|---|---|
| Pseudoephedrine Sulfate | 120–360 |
| Hydroxypropyl Methylcellulose 2208 100,000 cps | 160–480 |
| Ethylcellulose | 40–120 |
| Dibasic Calcium Phosphate Dihydrate | 56–164 |
| Povidone | 20–60 |
| Silicon Dioxide and | 6–12 |
| Magnesium Stearate | 2–6 |
| Matrix Core Weight Range: | 400–1200 mg | and b. a coating on said core comprising:

|  | mg/tablet |
|---|---|
| Loratadine | 5–15 |
| Hydroxypropyl Methylcellulose 2910 6 cps | 17–50 |
| Polyethylene Glycol 400 | 0.25–5.0 |
| Polyethylene Glycol 3350 | 3.4–10.15 |
| Approximate Coating Weight | 26–80.0 mg |
| Composition Weight Range | 427–1280 mg |

In a preferred aspects, the present invention provides film-coated extended release oral dosage composition comprising a a. a matrix core comprising:

|  | mg/core |
|---|---|
| Pseudoephedrine Sulfate | 240 |
| Hydroxypropyl Methylcellulose 2208 100,000 cps. | 160–480 |
| Ethylcellulose | 40–120 |
| Dibasic Calcium Phosphate Dihydrate | 56–164 |
| Povidone | 20–60 |
| Silicon Dioxide and | 6–12 |
| Magnesium Stearate | 2–6 |
| Approximate Core Weight Range | 520–1080 mg | and b. a coating on said core comprising:

|  | mg/tablet |
|---|---|
| Loratadine | 10 |
| Hydroxypropyl Methylcellulose 2910 6 cps. | 17–50 |
| Polyethylene Glycol 400 | 0.25–5.0 |
| Polyethylene Glycol 3350 | 3.4–10.15 |
| Approximate Coating Weight Range | 31–75 mg |
| Approximate Composition Weight Range | 552–1155 mg |

In a more preferred aspect, the present invention provides a film-coated extended release oral dosage composition comprising:

a. a matrix core

|  | mg/core |
|---|---|
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |
| Povidone USP | 40 |
| Silicon Dioxide NF and | 8 |
| Magnesium Stearate NF | 4 |
| Approximate Matrix Core weight | 800 mg | and b. a coating upon said core comprising:

|  | mg/tablet |
|---|---|
| Loratadine, Micronized | 10 |
| Hydroxypropyl Methylcellulose 2910 USP 6 cps | 33 |
| Polyethylene Glycol 400 NF | 0.67 |
| Polyethylene Glycol 3350 NF | 6.75 |
| Color Dispersion (Solids) | 6.25 |
| Approximate Coating Weight | 57 mg |
| Approximate Composition Weight | 857 mg |

DETAILED DESCRIPTION OF THE INVENTION

We have discovered a unique oral dosage composition containing a specific selection of ingredients including specific amounts of pseudoephedrine sulfate in a matrix core and of loratadine in an immediate release polymer film coating on the core. The oral dosage composition of this invention provides (1) immediate release (i.e., within one hour after oral administration to a patient) of the total dose of loratadine to maintain the once-a-day efficacy of Loratadine (2) the extended release of pseudoephedrine from the matrix polymer cover over a period of at least 12 preferably 12 to 16 hours and more preferably at least 16 hours from oral administration (3) reasonable dose size for enhancing patients' compliance and (4) a shelf life of at least 24 months.

In the course of development of the oral dosage composition of this invention, it was discovered that the selection of the polymers for the polymer matrix core was critical to achieve the desired extended release period of at least 12 hours, preferably 12 to 16 hours and more preferably for at least 16 hours for pseudoephedrine. For example, the use of hydroxypropyl methyl cellulose 4,000 cps and 15,000 cps did not provide this desired extended release period for dose of pseudoephedrine sulfate. Only by combining four parts by weight of hydroxypropyl methyl cellulose 2208 USP, 100,000 cps with one part by weight of ethyl cellulose together with ¼ part by weight of povidone as a secondary binder was the desired extended release profile for pseudoephedrine achieved. The matrix core also contains specific amounts of silicon dioxide as a glidant and magnesium stearate as a lubricant. The tablet hardness 22±6 Strong-Cobb Units (SCU) is not greatly affected by the higher level of lubricant (6 mg/tablet) but it is preferred to maintain the lubricant level at 1/10 part by weight of lubricant to one part by weight of povidone as secondary binder.

The hydroxyl propyl methyl cellulose 2910 acts as a film-forming agent in the film coating, and the polyethylene glycols act as plasticizers. Other suitable film-forming polymers which may be used include hydroxypropyl cellulose, methyl hydroxyethyl cellulose and sodium carboxymethyl cellulose.

The oral dosage composition of this invention also provides a shelf life of more than 24 months, e.g., up to 36 and 48 months so long as the tablets are stored in standard package at between 2° and 30° C. in an ambient environment.

In the preparation of the tablet core the povidone is dissolved in a mixture of alcohol and water. The pseudoephedrine sulfate, hydroxypropyl methylcellulose 2208 USP, 100,000 cps, ethylcellulose, and dibasic calcium phosphate are blended and granulated with the alcoholic water solution containing povidone. The granulation is milled, and dried to a loss on drying between 0.5 to 2.0%.

The dried granulation is milled and blended with requisite amounts of silicon dioxide and magnesium stearate. The final blend is compressed to produce the oral dosage composition in the preferred form of a tablet.

The coating is normally applied to the tablet cores in the following manner:

Cores are charged into a suitable coating pan. A water dispersion of hydroxypropyl methylcellulose 2910 USP and polyethylene glycol 3350 NF is applied to the cores. These sub-coated cores are then coated with a dispersion of loratadine, hydroxypropyl methylcellulose 2910 USP, polyethylene glycol 3350 NF and white color dispersion. This is followed by an application of polishing coating dispersion containing hydroxypropyl methylcellulose and polyethylene glycol 400 NF. The coated tablets are then branded (with black ink) and packaged in plastic bottles and blisters for storage at a temperature between 2° and 30° C. in an ambient environment

EXAMPLE I

This example illustrate preparation of the preferred oral dosage composition of this invention. The ingredients and specific amounts thereof are listed below.

1. Tablet Core
   A. Method of Manufacture
   1. Dissolve povidone in a mixture of alcohol and water.
   2. Combine the pseudoephedrine sulfate, hydroxypropyl methylcellulose 2208, ethylcellulose and dibasic calcium phosphate, dihydrate in a suitable mixing bowl and blend.
   3. Granulate the blend from Step 2 with the solution from Step 1. pass the wet granulation through a screen.
   4. Dry the granulation to a loss on drying between 0.5 to 2.0% as determined by a moisture balance or equivalent.
   5. Pass the dried granules through a screen.
   6. Add the requisite amount of silicon dioxide and magnesium stearate to the dried, milled granules and blend.
   7. Compress the blend on a suitable tablet press. During the compression operation, representative samples of the cores are taken and in-process tests are performed.

The core matrix meets the following specification:
Weight: 800±5% (mg)
Thickness: 0.280±0.010 inches
Hardness: 22±6 Strong-Cobb Units The cores are coated in the following manners:
A. Preparation of Coating Dispersions and Solutions
   1. Sub-Coating Solution
      (1) Disperse hydroxypropyl methylcellulose USP 2910 and polyethylene glycol 3350 in a portion of hot purified water.
      (2) Add the remainder of the purified water and cool the solution to room temperature.
   2. Active Coating Dispersion
      (1) Disperse hydroxypropyl methylcellulose USP 2910 and polyethylene glycol 3350 in a portion of hot purified water. Add additional water and cool the dispersion to room temperature.

(2) Disperse Loratadine in the remaining portion of room temperature purified water. Combine with hydroxypropyl methylcellulose polyethylene glycol dispersion (Step 1).
(3) Add white color dispersion. Mix until uniform.

3. Polishing Coating Solution
   (1) Disperse hydroxypropyl methylcellulose USP 2910 and polyethylene glycol 400 in a portion of hot purified water.
   (2) Add the remainder of the purified water and cool the solution to room temperature.

B. Coating of Tablet Core
   (1) Charge the requisite quantity of tablet cores to a suitable coating pan.
   (2) Apply the sub-coating solution.
   (3) Quantatively apply the active coating dispersion
   (4) Apply the polishing coating solution C Branding
   (1) Brand the coated tablets with black imprinting ink.

The preferred composition of the tablet core and coating is given below

| Tablet Core | mg/core |
|---|---|
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |
| Povidone USP | 40 |
| Silicon Dioxide NF | 8 |
| Magnesium Stearate NF | 4 |
| Approximate Core Weight | 800 mg |

| Tablet Coating | mg/tablet |
|---|---|
| Loratadine, Micronized | 10 |
| Hydroxypropyl Methylcellulose 2910 USP 6 cps | 33 |
| Polyethylene Glycol 400 NF | 0.67 |
| Polyethylene Glycol 3350 NF | 6.75 |
| Color Dispersion (Solids) | 6.25 |
| Imprinting Ink | — |
| Approximate Coating Weight | 57 mg |
| Approximate Tablet Weight | 857 mg |

The in vitro dissolution profile of the tablet of Example 1 was measured in a stirred 0.1N HCl solution at 37° C. The loratadine in the coating was dissolved within the first hour and the total dose of pseudoephedrine sulfate in the core was slowly released via erosion and dissolution mechanisms over a 12 to 16 hour period.

What is claimed is:

1. A film-coated extended release oral dosage composition comprising:
   a. a matrix core comprising:

| | mg/core |
|---|---|
| Pseudoephedrine Sulfate | 120–360 |
| Hydroxypropyl Methylcellulose 2208 100,000 cps | 160–480 |
| Ethylcellulose | 40–120 |
| Dibasic Calcium Phosphate Dihydrate | 56–164 |
| Povidone | 20–60 |
| Silicon Dioxide and | 6–12 |
| Magnesium Stearate | 2–6 |
| Matrix Core Weight Range: | 400–1200 mg | and b. a coating on said core comprising:

| | mg/tablet |
|---|---|
| Loratadine | 5–15 |
| Hydroxypropyl Methylcellulose 2910 6 cps | 17–50 |
| Polyethylene Glycol 400 | 0.25–5.0 |
| Polyethylene Glycol 3350 | 3.4–10.15 |
| Approximate Coating Weight Range: | 26–80.0 mg |
| Approximate Composition Weight Range: | 427–1280 mg |

2. A method of treating patients showing the signs and symptoms associated with upper respiratory diseases which comprises administering to such a patient the oral dosage composition of claim 1.

3. The oral dosage composition of claim 1 wherein 240 mg. of pseudoephedrine sulfate is in the core and 10 mg. of loratadine is in the coating.

4. A film-coated extended release oral dosage composition comprising:
   a. a matrix core comprising:

| | mg/core |
|---|---|
| Pseudoephedrine Sulfate | 240 |
| Hydroxypropyl Methylcellulose 2208 100,000 cps. | 160–480 |
| Ethylcellulose | 40–120 |
| Dibasic Calcium Phosphate Dihydrate | 56–164 |
| Povidone | 20–60 |
| Silicon Dioxide and | 6–12 |
| Magnesium Stearate | 2–6 |
| Approximate Core Weight Range: | 520–1080 mg | and b. a coating on said core comprising:

| | mg/tablet |
|---|---|
| Loratadine | 10 |
| Hydroxypropyl Methylcellulose 2910 6 cps. | 17–50 |
| Polyethylene Glycol 400 | 0.25–5.0 |
| Polyethylene Glycol 3350 | 3.4–10.15 |
| Approximate Coating Weight Range: | 31–75 mg |
| Approximate Composition Weight Range: | 552–1155 mg |

5. A method of treating a patient showing the signs and/or symptoms associated with upper respiratory diseases which comprises administering to such a patient the oral dosage form of claim 4.

6. A film-coated extended release oral dosage composition comprising:
   a. a matrix core comprising:

| | mg/core |
|---|---|
| Pseudoephedrine Sulfate USP | 240 |
| Hydroxypropyl Methylcellulose 2208 USP 100,000 cps | 320 |
| Ethylcellulose NF Type 7 | 80 |
| Dibasic Calcium Phosphate USP Dihydrate | 108 |
| Povidone USP | 40 |
| Silicon Dioxide and | 8 |
| Magnesium Stearate NF | 4 |
| Approximate Core weight | 800 mg | and b. a coating upon said core comprising:

|  | mg/tablet |
| --- | --- |
| Loratadine, Micronized | 10 |
| Hydroxypropyl Methylcellulose 2910 USP 6 cps | 33 |
| Polyethylene Glycol 400 NF | 0.67 |
| Polyethylene Glycol 3350 NF | 6.75 |
| Color Dispersion (Solids) | 6.25 |
| Approximate Coating Weight | 57 mg |

|  | mg/tablet |
| --- | --- |
| Approximate Composition Weight | 857 mg |

7. A method of treating a patient suffering from the signs and symptoms associated with upper respiratory disease and nasal congestion which comprises administering to such a patient the oral dosage composition of claim 6.

* * * * *